United States Patent
Keil

(10) Patent No.: US 9,468,389 B2
(45) Date of Patent: Oct. 18, 2016

(54) CONNECTION OF AN ELECTROCARDIOGRAM ELECTRODE TO A DATA ACQUISITION AND/OR TRANSFER FACILITY

(71) Applicant: Miriam Keil, Erlangen-Dechsendorf (DE)

(72) Inventor: Miriam Keil, Erlangen-Dechsendorf (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/686,339

(22) Filed: Apr. 14, 2015

(65) Prior Publication Data

US 2015/0311624 A1    Oct. 29, 2015

(30) Foreign Application Priority Data

Apr. 15, 2014  (DE) .......................... 10 2014 207 242

(51) Int. Cl.
*H01R 4/28* (2006.01)
*A61B 5/0408* (2006.01)
*H01R 11/24* (2006.01)
*A61B 5/0402* (2006.01)

(52) U.S. Cl.
CPC ............. *A61B 5/0408* (2013.01); *H01R 11/24* (2013.01); *A61B 5/0402* (2013.01); *A61B 2562/227* (2013.01); *H01R 2201/12* (2013.01)

(58) Field of Classification Search
CPC .. H01R 13/62; H01R 11/24; H01R 2201/12; A61B 5/0408; A61B 2562/227; A61B 5/0402
USPC .......................... 439/345, 725–729, 310, 909
See application file for complete search history.

(56) References Cited

U.S. PATENT DOCUMENTS

| 6,780,065 | B2 * | 8/2004 | Schwarz | ................ A61N 1/048 439/310 |
|---|---|---|---|---|
| 2003/0228805 | A1 | 12/2003 | Schwarz | |
| 2008/0012568 | A1 | 1/2008 | Kwapil et al. | |
| 2009/0062636 | A1 | 3/2009 | Muz | |

FOREIGN PATENT DOCUMENTS

| DE | 10225621 B3 | 1/2004 |
|---|---|---|
| DE | 102004037375 A1 | 3/2006 |
| DE | 102007059096 A1 | 6/2009 |
| DE | 102009057968 A1 | 8/2011 |

OTHER PUBLICATIONS

German Office Action for German Application No. 10 2014 207 242.5, mailed Nov. 13, 2014, with English Translation.

* cited by examiner

*Primary Examiner* — Javaid Nasri
(74) *Attorney, Agent, or Firm* — Lempia Summerfield Katz LLC

(57) ABSTRACT

A connection facility for connecting an electrocardiogram electrode to a data acquisition and/or transfer facility includes a signal line and a connecting element for connecting the signal line to the electrocardiogram electrode. The connecting element has a clamping body with two clamping jaws connected by an elastic reset element between a front and a rear end of the clamping body, and a contact element for making contact with the electrocardiogram electrode arranged at the front end of the clamping body and connected in an electrically conducting manner to the signal line. The connecting element has a grip region, in which the jaw width is wider than the jaw width at the front end. The contact element is arranged centrally in the jaw width of the clamping jaws and has an extension in the direction of the jaw width, which is smaller than the jaw width at the front end.

14 Claims, 1 Drawing Sheet

CONNECTION OF AN ELECTROCARDIOGRAM ELECTRODE TO A DATA ACQUISITION AND/OR TRANSFER FACILITY

This application claims the benefit of DE 102014207242.5, filed on Apr. 15, 2014, which is hereby incorporated by reference in its entirety.

FIELD

The disclosed embodiments relate to a connection facility for connecting an electrocardiogram electrode to a data acquisition and/or transfer facility.

BACKGROUND

Electrocardiogram electrodes are used to detect heart movement in a plurality of medical diagnostic procedures. The detection of heart movement is warranted for synchronization between the cardiac cycle and data acquisition in examination procedures that use imaging, such as for example CT and MR tomography. For the purposes of such examinations, self-adhesive electrodes are attached to the patient, being connected to data acquisition and/or transfer facilities by connecting cables. This allows small and light transfer facilities to be used, which are supported on the patient and connected to the electrocardiogram electrodes and transmit the measurement data or trigger signals to further measuring or control facilities.

To connect the electrodes to the data acquisition and/or transfer facility, connection facilities are used, which have a clamp-type connecting element at one end of a signal line and a coupling element for connecting to the data acquisition and/or transfer facility at the other end. At the front end of a clamping body, the connecting element has contact elements for making contact with the electrocardiogram electrode. The signal line is passed at a right angle to the clamping jaws of the clamping body, making it convenient to position the connecting elements on the electrocardiogram electrodes when the connecting elements are applied from the right side of the couch using the right hand.

The structure of the connecting element makes it difficult to position in this manner from the left side of the couch or using the left hand.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the disclosed embodiments may provide a connection facility for connecting an electrocardiogram electrode to a data acquisition and/or transfer facility, which is easier to manipulate when contact is not to be made with an electrocardiogram electrode from the right side of the couch and/or with the right hand. The connection facility includes a signal line and a connecting element for connecting the signal line to the electrocardiogram electrode. The connecting element has a clamping body with two clamping jaws connected by an elastic reset element between a front and rear end of the clamping body and a contact element for making contact with the electrocardiogram electrode arranged at the front end of the clamping body and connected in an electrically conducting manner to the signal line.

In one aspect of the connection facility, the connecting element has a grip region, in which the jaw width is wider than the jaw width at the front end of the clamping body, the contact element being arranged in the center of the jaw width of the clamping jaws and having an extension in the direction of the jaw width, which is smaller than the jaw width at the front end of the clamping body.

According to one aspect, the contact element, which makes contact with the electrocardiogram electrode, is arranged in the center of the jaw width of the clamping jaws. As a result, when the connecting element rests on a patient, the contact element is halfway up the connecting element in the front region. Provision is also made for the jaw width in the front region of the clamping body to be narrower than in a grip region. As a result, the overall height of a connecting element resting on a patient is shorter in the front region of the clamping body than in the grip region. As a result, the connecting element of the connection facility may be arranged on a patient in two different ways. The side of the connecting element facing the patient in a first arrangement may face away from the patient in the second arrangement, and the side that previously faced away may rest on the patient. Because the contact element is arranged centrally in relation to the jaw width, the distance between the contact element and the patient or the electrocardiogram electrode with which contact is to be made is identical in both instances. Contact with the electrocardiogram electrode may therefore be achieved equally well in both instances.

Because the connecting element may be arranged on the electrocardiogram electrode or the patient with two different orientations, the signal line may be passed in two mirror-symmetrical ways. The connection facility therefore allows easier connection of the connecting element to the electrocardiogram electrode from both directions or with both hands.

The use of a narrow contact element, which does not extend over the entire jaw width, reduces the conductive regions on the connecting element, thereby improving suitability for use in a magnetic resonance facility. The contact element may be formed, for instance, from two half shells, one half shell in each instance being arranged on one of the clamping jaws. Without external pressure on the clamping jaws the clamping jaws are pressed together by the reset element at the front end of the clamping body. The pressing together of the clamping jaws causes the two half shells of the contact element to be brought together to form an essentially round recess, in which a contact element of an electrocardiogram electrode may engage. A pressure on the clamping jaws in the grip region, which is located beyond the reset element when viewed from the front end of the clamping body, allows the clamping jaws at the front end of the clamping body and therefore the half shells of the contact element to be parted in order to grip the contact element of the electrocardiogram electrode.

The clamping jaws in the connection facility may be longer than the clamping jaws are wide. For example, the length of the clamping jaw may be at least 1.5 times the width of the clamping jaw. This allows the clamping jaws to be configured as identical or with mirror symmetry to one another.

The jaw width in the connection facility at the front end of the clamping body may be at least 20%, e.g., at least 40%, narrower than the jaw width in the grip region. The grip region is arranged, for instance, at the rear end of the clamping body. The shape of the clamping jaws means that the connecting element may be manipulated easily, providing both a narrow front end of the clamping body and therefore easy contact with the electrocardiogram electrode even when the contact element is relatively narrow. The clamping jaws may, for instance, be essentially trapezoidal, it being possible for the clamping jaws to form, for instance, an isosceles trapezoid.

The contact element may extend over at most half, e.g., over at most a third, of the distance between the front end of the clamping body and the reset element. It is also possible for the contact element to extend over a quarter of the distance or over a shorter length.

The signal line may pass out of the clamping body at the rear end of the clamping body. The signal line may pass out of the clamping body at an angle of at least 20°, e.g., at least 40°, to the longitudinal direction of a clamping jaw. Alternatively or additionally, the signal line may pass out of the clamping body at an angle of at most 70°, e.g., at most 50°, to the longitudinal direction of a clamping jaw. The signal line passes out of the clamping body essentially at a right angle to the direction of the jaw width. When a flexible signal line is used, the specified angles for the passage of the signal line out of the clamping body establish the angle at the point where the signal line exits from the clamping body or the clamping jaw. The described passage of the signal line improves the ability of the connection facility to be manipulated and/or the passage allows a shorter signal line to be used for connection to a data acquisition and/or transfer facility.

The connection facility may be made of essentially non-magnetic material. The material may have no ferromagnetism and at least no powerful paramagnetism. Using non-magnetic materials, for example copper, as conductors, improves compatibility with magnetic resonance facilities. For the same reason, the clamping body may be made of insulating material, such as plastic.

DETAILED DESCRIPTION

Figure 1:
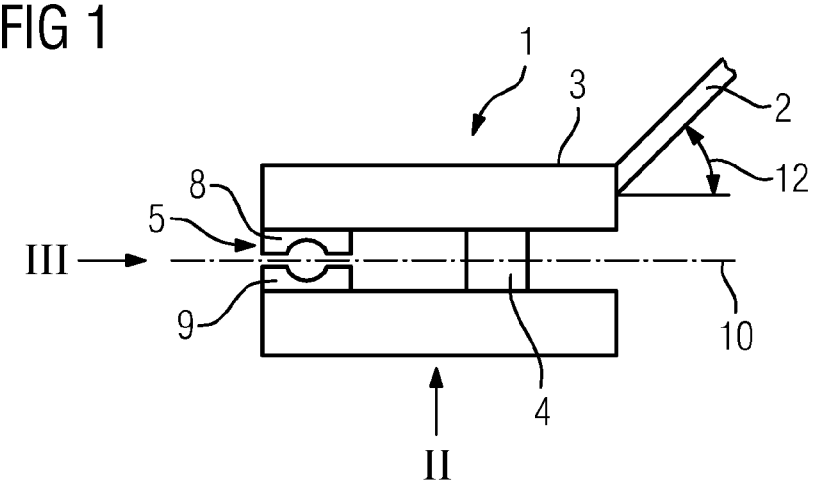
FIG. 1 shows a schematic diagram of an exemplary embodiment of a connection facility in accordance with one embodiment.
Figure 2:
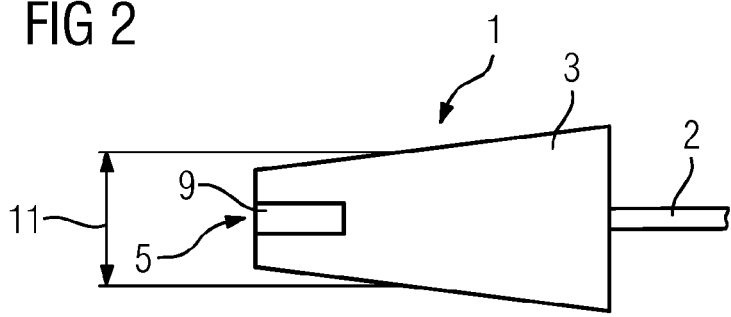
FIG. 2 shows a schematic diagram of a second view of the connection facility shown in FIG. 1.
Figure 3:
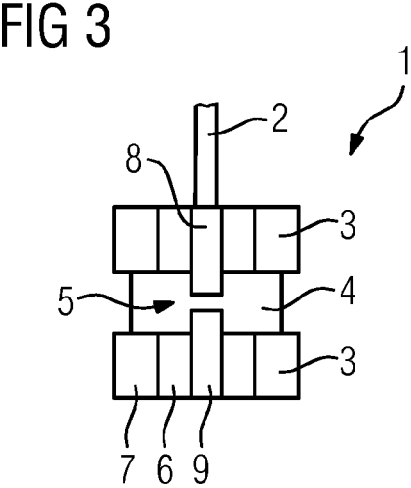
FIG. 3 shows a schematic diagram of a third view of the connection facility shown in FIGS. 1 and 2.

FIGS. 1, 2 and 3 show three different views of an exemplary embodiment of a connection facility for connecting an electrocardiogram electrode to a data acquisition and/or transfer facility. The viewing directions of the representations shown in FIGS. 2 and 3 are marked by arrows II and III in FIG. 1.

The connection facility includes a signal line 2 and a connecting element 1 for connecting the signal line 2 to an electrocardiogram electrode in an electrically conducting manner. Arranged at the second end (not shown) of the signal line 2 is a coupling element for coupling the connection facility to a data acquisition and/or transfer facility. The nature of the coupling, for example whether it is a plug or a socket, depends on the nature of the data acquisition and/or transfer facility and may be adapted in any manner to the features of the application.

The connecting element 1 includes a clamping body and a contact element 5 for making contact with the electrocardiogram electrode arranged at a front end of the clamping body and connected in an electrically conducting manner to the signal line 2. The clamping body includes two clamping jaws 3, which are connected by a reset element 4. The clamping jaws 3 and the reset element 4 are formed from a material that is compatible with magnetic resonance facilities. The reset element 4 is configured as an elastically deformable block, made for example of plastic, that presses together the clamping jaws 3 in the front region of the clamping body. Pressing on the clamping jaws 3 in a grip region behind the reset element 4 allows the clamping jaws 3 in the front region to be parted and to return to the relative position predetermined by the reset element 4 when the grip region is released. In alternative embodiments, the reset force may be increased by an additional spring element, which is arranged in the region between the reset element 4 and the rear end of the clamping body between the clamping jaws 3. The additional spring element may be configured for example as a helical spring. The additional spring element may be formed from plastic. Sufficient deformability and, for instance, elasticity of the reset element 4 or the additional spring element and adequate rigidity of the clamping jaws 3 may be achieved by corresponding selection of material and shape.

As shown in the example of FIG. 2, the clamping jaws 3 have the shape of an isosceles trapezoid. The region 6 of the clamping jaw 3 shown in FIG. 3 is at a right angle to the viewing direction in FIG. 3 and the region 7 runs obliquely to the rear in FIG. 3. The region between the reset element 4 and the rear end of the clamping body, at which the signal line 2 passes out of the clamping body, forms the grip region, in which the clamping jaws 3 are configured as relatively wide.

Arranged in the front region of the clamping body is a contact element 5, which is formed by the two half shells 8, 9 made of copper. The signal line 2 is passed through the clamping jaw 3 to the half shell 8 and makes contact therewith. The half shells 8, 9 are connected to the clamping jaw 3 by being partially embedded or incorporated into the clamping jaw 3. The segment of the signal line 2 passed through the clamping jaw 8 is also incorporated into the clamping jaw 3. Alternatively, a recess may be provided in the clamping jaw 3, through which the signal line 2 is passed, e.g., being clamped therein.

To connect the connecting element 1 to an electrocardiogram electrode, a user may first press the clamping body together in the grip region, in order to separate the two half shells 8, 9 and introduce a, for example pin-like, contact region of the electrocardiogram electrode between the half shells 8, 9. The half shells 8, 9 are then pressed together by the reset element 4 by the clamping jaws 3 and make contact with the connecting region of the electrocardiogram electrode.

As shown in FIG. 2 and FIG. 3, the half shells 8, 9 in the illustrated connection facility each extend completely through the clamping jaw 3 in the direction of the arrow II. In alternative embodiments of the connection facility, the extension of the half shells 8, 9 or of the contact element 5 in this direction may be reduced in order to reduce conductive surfaces of the connection facility further.

The signal line 2 passes out of the clamping jaw 3 and therefore out of the clamping body at an angle 12, as shown in FIG. 1, of approximately 45° to the longitudinal direction of the clamping jaw 3 and at a right angle to the direction of the jaw width. The central arrangement of the contact element 5 in the width of the clamping jaw 3 as indicated by the double arrow 11 and the tapering of the clamping jaw 3 toward the front end establish that the illustrated connection facility may make contact with a contact element of an electrocardiogram electrode in two different ways. Contact may be made with an electrocardiogram electrode with associated contact element such that it is arranged above or below the connecting element 1 in FIG. 3, with the result that a contact element of the electrocardiogram electrode engages between the half shells 8, 9 from above or from below. The connection facility may be arranged correspondingly on a patient, as shown in FIG. 1. However, the connecting element 1 may be rotated, thereby mirroring the representation illustrated in FIG. 1 about the axis 10. The signal line 2 may therefore pass both to the left and also to the right in relation to the axis 10, thereby allowing the connection facility to be positioned easily from both sides of a patient or with both hands.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A connection facility for connecting an electrocardiogram electrode to a data acquisition facility, a transfer facility, or both a data acquisition facility and a transfer facility, the connection facility comprising:
    a signal line;
    a connecting element configured to connect the signal line to the electrocardiogram electrode, the connecting element comprising:
        a clamping body comprising two clamping jaws held in a clamped position and connected by an elastic reset element between a front end of the clamping body and a rear end of the clamping body;
        a contact element configured to make contact with the electrocardiogram electrode arranged at the front end of the clamping body using the two clamping jaws and connected in an electrically conducting manner to the signal line; and
        a grip region in which a jaw width of the clamping jaws is wider than a jaw width of the clamping jaws at the front end of the clamping body,
    wherein the contact element is arranged centrally in the jaw width of the clamping jaws.

2. The connection facility of claim 1, wherein the jaw width at the front end of the clamping body is at least 20% narrower than the jaw width in the grip region.

3. The connection facility of claim 1, wherein the contact element extends over at most half of the distance between the front end of the clamping body and the reset element.

4. The connection facility of claim 1, wherein the signal line passes out of the clamping body at the rear end of the clamping body.

5. The connection facility of claim 1, wherein the signal line passes out of the clamping body at an angle of at least 20° to a longitudinal direction of one of the two clamping jaws.

6. The connection facility of claim 1, wherein the signal line passes out of the clamping body at an angle of at most 70° to a longitudinal direction of one of the two clamping jaws.

7. The connection facility of claim 1, wherein the connection facility is made of non-magnetic material.

8. The connection facility of claim 1, wherein the clamping body is made of insulating material.

9. The connection facility of claim 1, wherein the jaw width at the front end of the clamping body is at least 40% narrower than the jaw width in the grip region.

10. The connection facility of claim 1, wherein the contact element extends over at most a third of the distance between the front end of the clamping body and the reset element.

11. The connection facility of claim 1, wherein the signal line passes out of the clamping body at an angle of at least 40° to a longitudinal direction of one of the two clamping jaws.

12. The connection facility of claim 1, wherein the signal line passes out of the clamping body at an angle of at most 50° to a longitudinal direction of one of the two clamping jaws.

13. The connection facility of claim 1, wherein the clamping body is made of plastic.

14. The connection facility of claim 1, wherein the connecting element is configured to connect to the electrocardiogram electrode in a first alignment and a second alignment, wherein the second alignment is rotated 180 degrees from the first alignment around the signal line.

* * * * *